United States Patent
Matsumoto

(10) Patent No.: US 8,777,866 B2
(45) Date of Patent: Jul. 15, 2014

(54) PULSE RATE COUNTING DEVICE, PULSE RATE COUNTING METHOD, AND RECORD MEDIUM THEREFOR

(75) Inventor: Chikako Matsumoto, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1050 days.

(21) Appl. No.: 12/399,258

(22) Filed: Mar. 6, 2009

(65) Prior Publication Data
US 2009/0227879 A1 Sep. 10, 2009

(30) Foreign Application Priority Data
Mar. 6, 2008 (JP) .................... 2008-056418

(51) Int. Cl.
*A61B 5/08* (2006.01)

(52) U.S. Cl.
USPC .............. 600/500; 600/501; 600/502

(58) Field of Classification Search
USPC ................................. 600/500–503
See application file for complete search history.

(56) References Cited

U.S. PATENT DOCUMENTS

| | | | | |
|---|---|---|---|---|
| 3,575,162 A | * | 4/1971 | Gaarder | 600/479 |
| 4,338,950 A | * | 7/1982 | Barlow et al. | 600/500 |
| 5,759,156 A | * | 6/1998 | Hayakawa et al. | 600/483 |
| 6,810,277 B2 | * | 10/2004 | Edgar et al. | 600/336 |

FOREIGN PATENT DOCUMENTS

JP  9-154825 A  6/1997

* cited by examiner

*Primary Examiner* — Navin Natnithithadha
*Assistant Examiner* — Michael R Bloch
(74) *Attorney, Agent, or Firm* — Fujitsu Patent Center

(57) ABSTRACT

A pulse rate counting device includes: a short-term average value calculation unit for calculating an average interval of predetermined previous pulses; a fluctuation amount calculation device for calculating the amount of fluctuation on the basis of the difference between the average interval and an actual pulse wave interval; a search range determination unit for calculating the width of the search range, calculating an amount of displacement on the basis of a time change of the average interval, and determining as a search range a range including an appearance prediction value of the next detection point calculated from the average interval and indicated by the width of the search range from a starting point determined on the basis of the amount of displacement; and a pulse wave interval detection unit for detecting the detection point in the determined search range, and outputting a pulse wave interval.

14 Claims, 14 Drawing Sheets

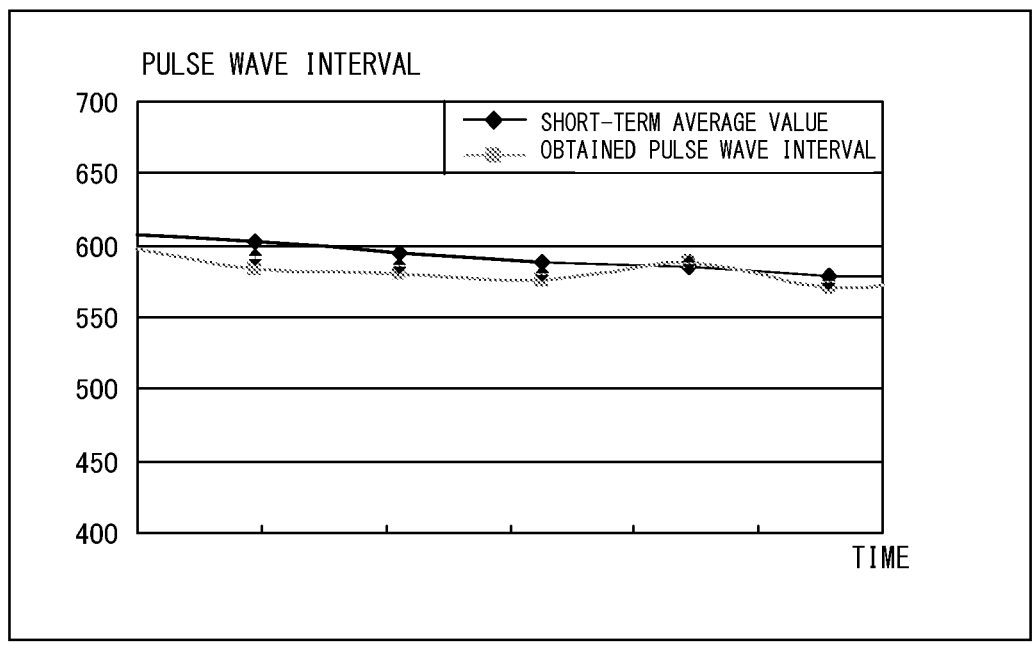
F I G. 3

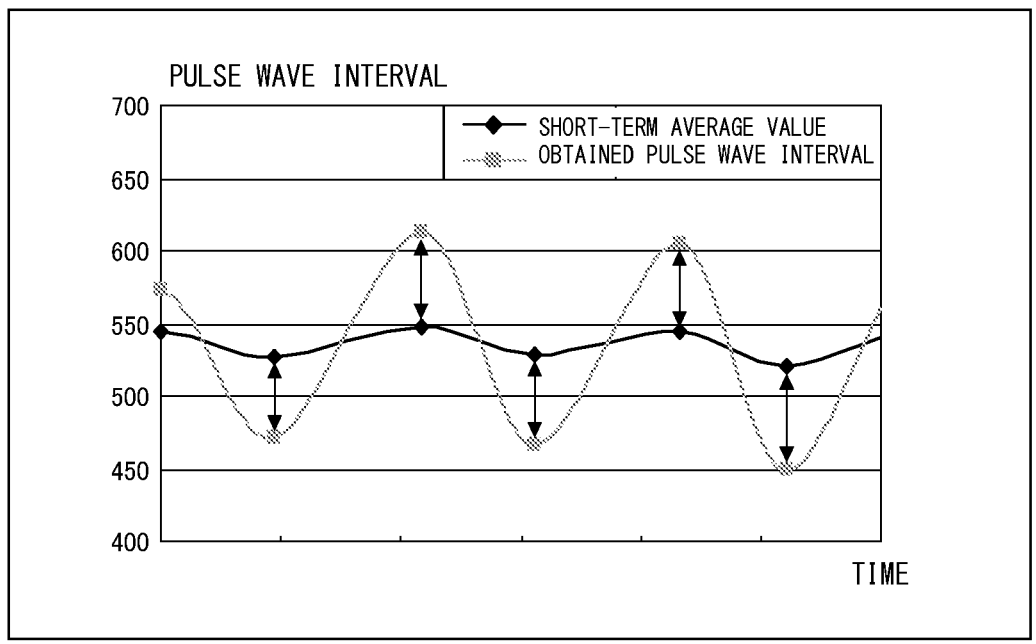
F I G. 4

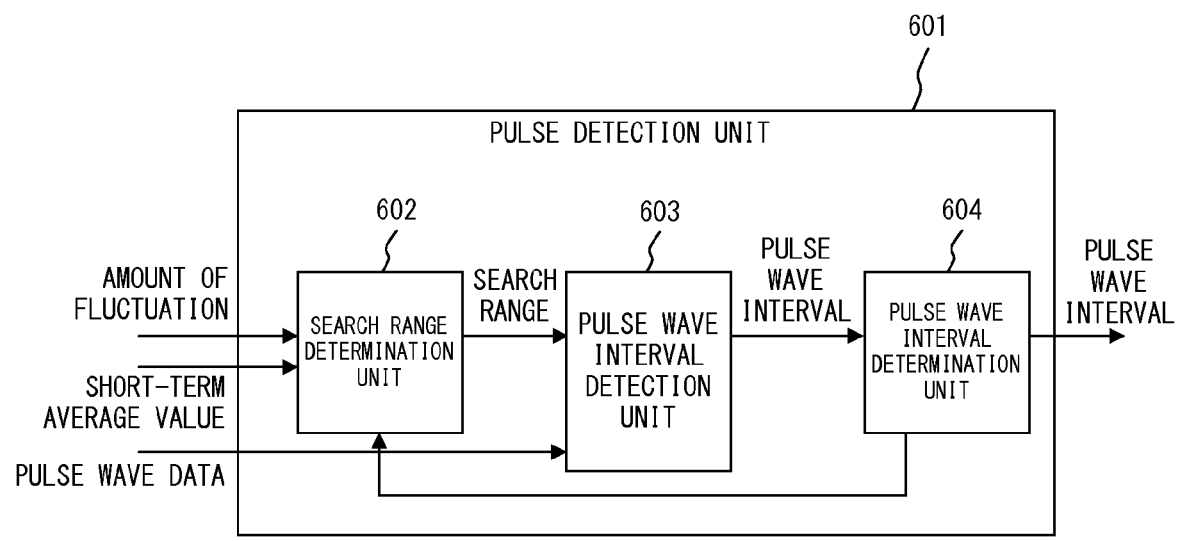
F I G. 7

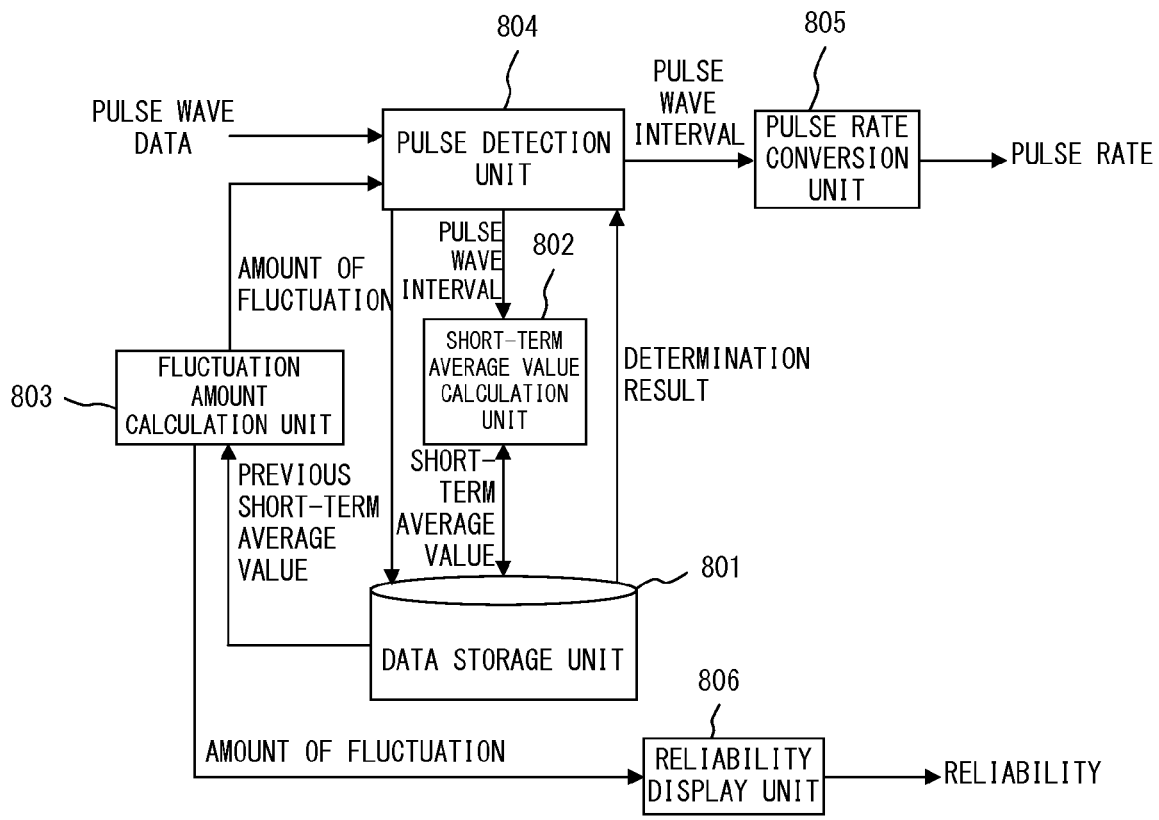
F I G. 9

| No. | AAI | SHORT-TERM AVERAGE VALUE | LONG-TERM AVERAGE VALUE | AMOUNT OF FLUCTUATION | AAI DETERMINATION RESULT | RE-SEARCHING YES/NO |
|---|---|---|---|---|---|---|
| 1 | 640 | 640 | 640 | 0 | 0 | 0 |
| 2 | 651 | 645 | 645 | 0.001 | 0 | 0 |
| 3 | 619 | 637 | 637 | 0.002 | 0 | 0 |
| ... | | | | | | |
| 50 | 738 | 697 | 656 | 0.069 | 4 | 1 |
| 51 | 873 | 707 | 655 | 0.107 | 3 | 1 |
| 52 | 662 | 703 | 662 | 0.109 | 5 | 0 |
| 53 | 750 | 699 | 675 | 0.089 | 0 | 0 |
| 54 | 711 | 715 | 674 | 0.086 | 0 | 0 |
| ... | | | | | | |

AAI DETERMINATION RESULT EXAMPLES
    0: NO PROBLEM
    1: NO OPTIMUM VALUE AFTER RE-SEARCHING
    2: MINIMUM VALUE FORWARD INITIAL SEARCH RANGE AS
       RESULT OF RE-SEARCHING
    3: MINIMUM VALUE BACKWARD INITIAL SEARCH RANGE AS
       RESULT OF RE-SEARCHING
    4: CORRECTION BY DIFFERENCE BETWEEN PULSE WAVE
       INTERVAL AND LONG-TERM AVERAGE VALUE
    5: CORRECTION BY DIFFERENCE BETWEEN SHORT-TERM
       AVERAGE VALUE AND LONG-TERM AVERAGE VALUE

FIG. 12

PULSE RATE COUNTING DEVICE, PULSE RATE COUNTING METHOD, AND RECORD MEDIUM THEREFOR

BACKGROUND OF THE INVENTION

1. Field of the Invention

The present invention relates to a heart rate counting device, and more specifically to a pulse rate counting device which obtains a pulse rate with high accuracy from unstable pulse wave data acquired during physical activity etc.

2. Description of the Related Art

Conventionally, a device for obtaining a pulse rate using a pulse wave sensor attached to the ear or finger of a user has become commercially practical as heart rate counting technology requiring smaller load for the user than electrocardiograph.

Pulse wave data is stable when the quantity of motion is small during walking etc. (refer to FIG. 1A), and can be used for detecting a pulse wave interval with high accuracy. However, the pulse wave data becomes unstable when the quantity of motion is large during running etc. (refer to FIG. 1B), and it is difficult to detect a pulse wave interval with high accuracy.

Therefore, in the conventional technology, a pulse rate is obtained using two sensors, that is, a pulse wave sensor and a physical activity sensor for detecting the physical activities as a physical activity signal using an acceleration sensor (for example, refer to the patent document 1) to solve the problem of unstable pulse waves caused by a large change in the pulse rate during physical activity.

However, in the conventional system, the physical activity sensor is required in addition to the pulse wave sensor, thereby causing the problem of increasing the load for a user in price and attaching operation.

Since there is less unstable pulse waves during resting or during moderate physical activity, the change in heart rate can be roughly classified into three levels, that is, a stable status, an increasing tendency, and a decreasing tendency, and the subsequent heart rate can be predicted depending on the current tendency.

During fast walking or running effective as aerobic exercise, there occurs more unstable pulse wave due to the physical activities, the displacement of a sensor, etc. Therefore, there occur various fluctuations such as repetitions of small changes in the waveform intervals in pulse waves, repetitions of increase and decrease in amplitude, etc., thereby causing the problem that it is difficult to detect a correct pulse only by determining an increasing tendency or decreasing tendency acquired from a simple average value of a previous measurement result.

[Patent Document 1] Japanese Published Patent Application No. H9-154825

SUMMARY OF THE INVENTION

The present invention aims at providing a pulse rate counting device capable of detecting a pulse wave interval only from a signal of a pulse wave sensor, and obtaining a heart rate with high accuracy.

The feature of the pulse rate counting device includes: a short-term average value calculation unit for receiving input of pulse wave data acquired from a change of bloodstream and calculating an average interval of predetermined previous pulses; a fluctuation amount calculation unit for calculating the amount of fluctuation on the basis of the difference between the average interval and an actual pulse wave interval; a search range determination unit for calculating the width of the search range of a detection point as a reference of the next pulse wave interval on the basis of the previous pulse wave interval and the amount of fluctuation, calculating an amount of displacement on the basis of a time change of the average interval, and determining as a search range a range including an appearance prediction value of the next detection point calculated from the average interval and indicated by the width of the search range from a starting point determined on the basis of the amount of displacement in a range; and a pulse wave interval detection unit for detecting the detection point in the determined search range, and outputting an interval between the predetermined detection point and a current detection point as a pulse wave interval.

Using the disclosed device, the cost of the device can be reduced and a pulse rate can be measured with high accuracy.

BRIEF DESCRIPTION OF THE DRAWINGS

FIG. 3 is a graph of a short-term average value when the fluctuation of pulse waves is small and a pulse wave interval;

FIG. 4 is a graph of a short-term average value when the fluctuation of pulse waves is large and a pulse wave interval;

FIG. 7 shows the configuration of the pulse detection unit of the pulse rate counting device according to the third embodiment of the present invention;

FIG. 9 shows the principle of the pulse rate counting device according to the fifth embodiment of the present invention;

FIG. 12 shows an example of data stored in the data storage unit; and

DESCRIPTION OF THE PREFERRED EMBODIMENTS

The embodiments of the present invention are described below with reference to the attached drawings.

Figure 1A:
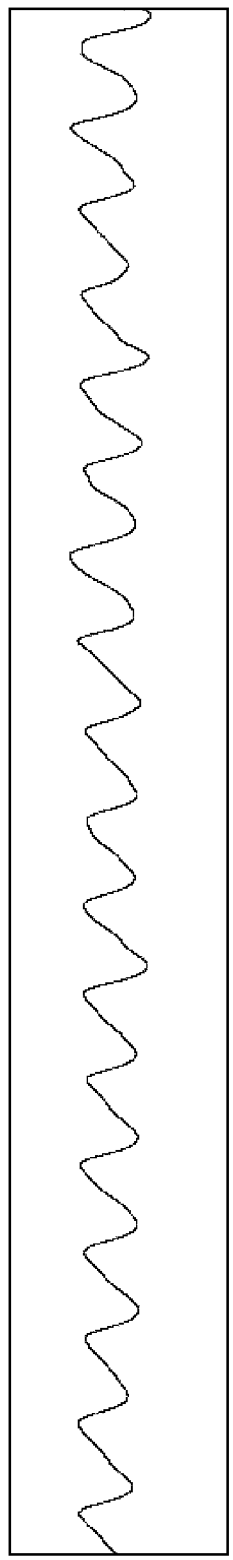
FIG. 1A shows pulse wave data during walking.
Figure 1B:
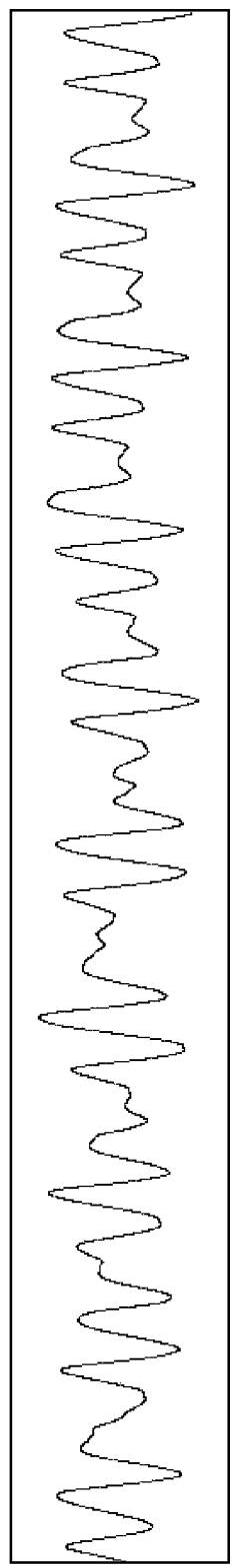
FIG. 1B shows pulse wave data during running.
Figure 2:
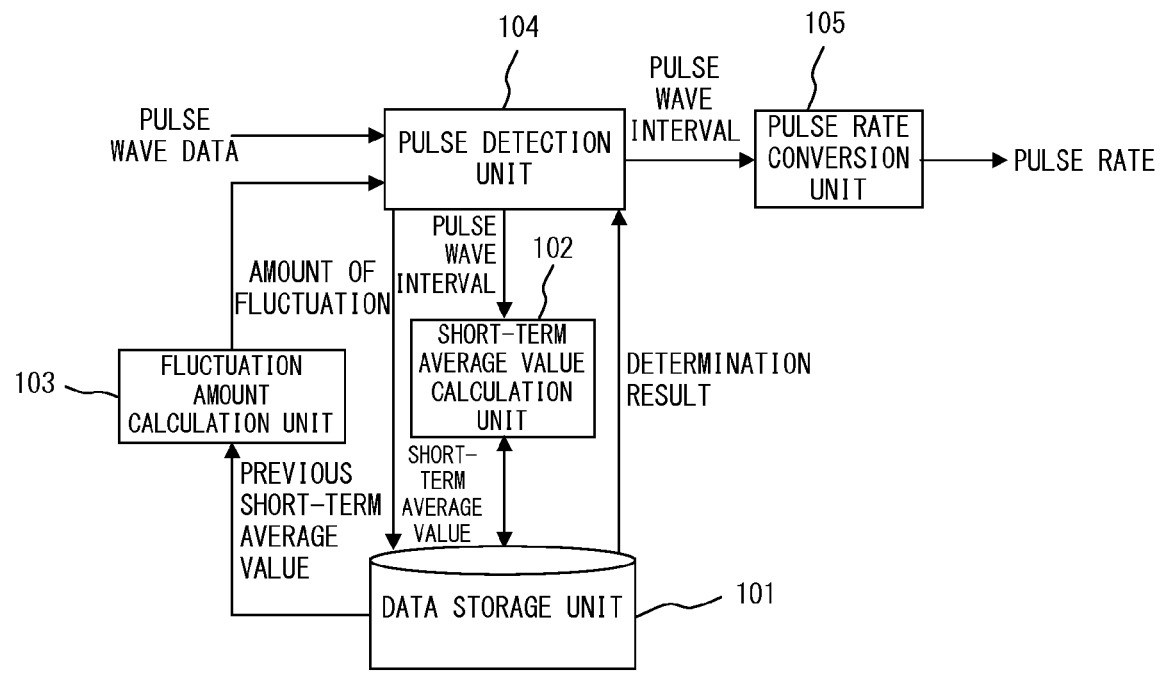
FIG. 2 shows the principle of the pulse rate counting device according to the first embodiment of the present invention.

FIG. 2 shows the principle of the pulse rate counting device according to the first embodiment of the present invention.

The pulse rate counting device according to the first embodiment of the present invention includes a data storage unit 101, a short-term average value calculation unit 102, a fluctuation amount calculation unit 103, a pulse detection unit 104, and a pulse rate conversion unit 105.

The data storage unit 101 stores a previously obtained pulse wave interval, and a past short-term average value.

The short-term average value calculation unit 102 calculates an average value of the pulse wave interval of some previous pulses for a pulse wave interval to be obtained. A calculation result is stored in the data storage unit 101 as a short-term average value.

The fluctuation amount calculation unit 103 calculates an amount of fluctuation corresponding to the fluctuation of the pulse wave data from the absolute value of the difference between the past short-term average value and pulse wave interval. FIG. 3 is a graph showing the short-term average value and the obtained pulse wave interval when the fluctuation of pulse wave is small, and FIG. 4 is a graph showing the short-term average value and the obtained pulse wave interval when the fluctuation of pulse wave is large. The value of |short-term average value (i)−obtained pulse wave interval (i)| stored for a predetermined time in the graph is referred to as an amount of fluctuation. In the case shown in FIG. 3 in which the fluctuation of pulse waves is small, the amount of fluctuation is small. In the case shown in FIG. 4 in which the fluctuation of pulse waves is large, the amount of fluctuation is large.

When the pulse wave data is input to the pulse detection unit 104, the pulse detection unit 104 detects the pulse wave interval to be next obtained from the short-term average value and the amount of fluctuation. The pulse wave data is obtained on the basis of a change in bloodstream.

The pulse rate conversion unit 105 performs a conversion into a pulse rate from the pulse wave interval calculated by the pulse detection unit 104 and the sampling frequency of the pulse wave data.

Figure 5:
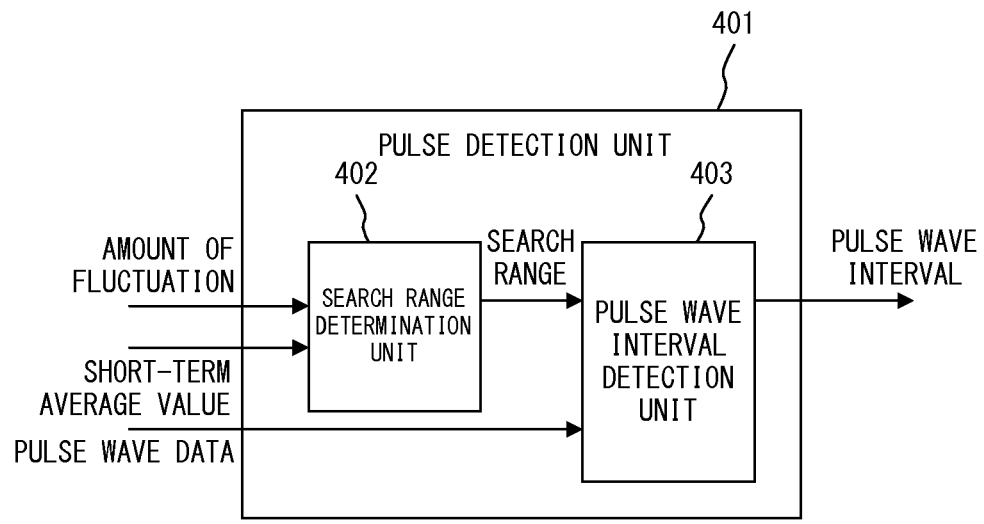
FIG. 5 shows the configuration of the pulse detection unit of the pulse rate counting device according to the second embodiment of the present invention.

FIG. 5 shows the configuration of the pulse detection unit of the pulse rate counting device according to the second embodiment of the present invention.

Figure 6:
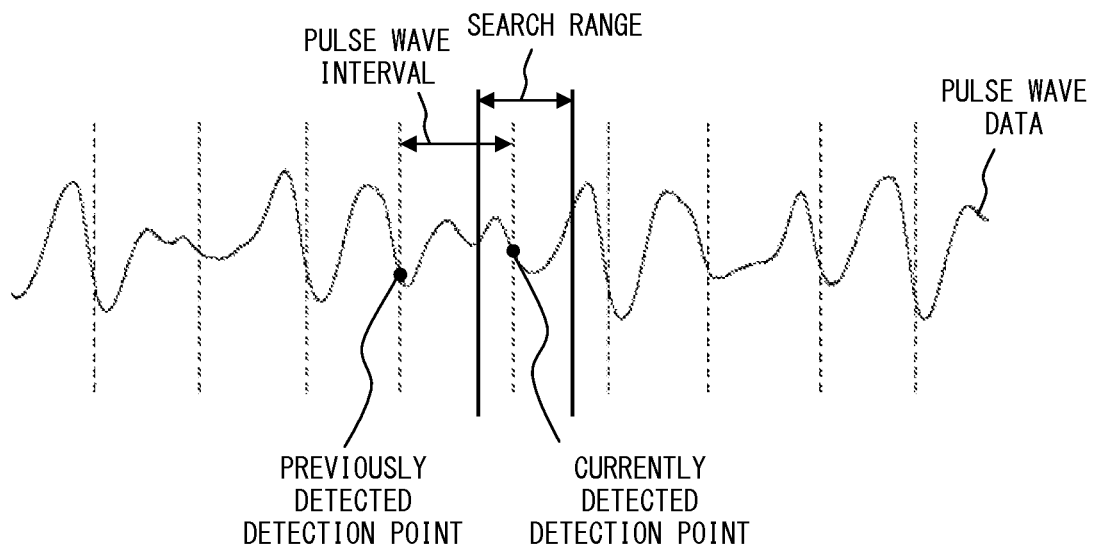
FIG. 6 shows pulse wave data.

FIG. 6 shows the pulse wave data with the search range, the pulse wave interval, and the detection point.

The pulse detection device according to the second embodiment includes a data storage unit, a short-term average value calculation unit, a fluctuation amount calculation unit, a pulse detection unit 401, and a pulse rate conversion unit.

The basic configuration of the pulse detection device according to the second embodiment is similar to that of the pulse detection device according to the first embodiment of the present invention.

The pulse detection unit 401 includes a search range determination unit 402 and a pulse wave interval detection unit 403.

The search range determination unit 402 determines a search range of a detection point (refer to FIG. 6) as a reference of the pulse wave interval to be obtained next on the basis of the short-term average value and the amount of fluctuation.

The pulse wave interval detection unit 403 detects the detection point as a reference of the pulse wave interval in the search range of the pulse wave data. The interval between the previously detected detection point and the currently detected detection point is stored as a pulse wave interval in the data storage unit. A detection point can be a minimum value or the maximum value in a search range, a minimum value or the maximum value of the difference data of pulse wave data, etc.

FIG. 7 shows the configuration of the pulse detection unit of the pulse rate counting device according to the third embodiment of the present invention.

Like the first pulse detection device, the pulse detection device according to the third embodiment includes a data storage unit, a short-term average value calculation unit, a fluctuation amount calculation unit, a pulse detection unit 601, and a pulse rate conversion unit.

The basic configuration of the pulse detection device according to the third embodiment is similar to the pulse detection device according to the first embodiment of the present invention.

The pulse detection unit 601 includes a search range determination unit 602, a pulse wave interval detection unit 603, and a pulse wave interval determination unit 604.

The search range determination unit 602 determines a search range of a detection point as a reference of the pulse wave interval to be obtained next on the basis of a short-term average value and an amount of fluctuation.

The pulse wave interval detection unit 603 detects a detection point as a reference of a pulse wave interval in a search range. The interval between the previously obtained detection point and the currently obtained detection point is output as a pulse wave interval to the pulse wave interval determination unit 604.

The pulse wave interval determination unit 604 determines whether or not the obtained pulse wave interval is an appropriate value.

If it is determined that the interval is an appropriate value, the pulse wave interval determination unit 604 stores the pulse wave interval in the data storage unit.

If it is determined that the interval is an inappropriate value, the determination result is output to the search range determination unit 602, and the search range determination unit 602 sets again a search range, and detects a pulse wave interval again. The pulse wave interval detected after setting again the search range is stored as a pulse wave interval searched again in the data storage unit.

Figure 8:
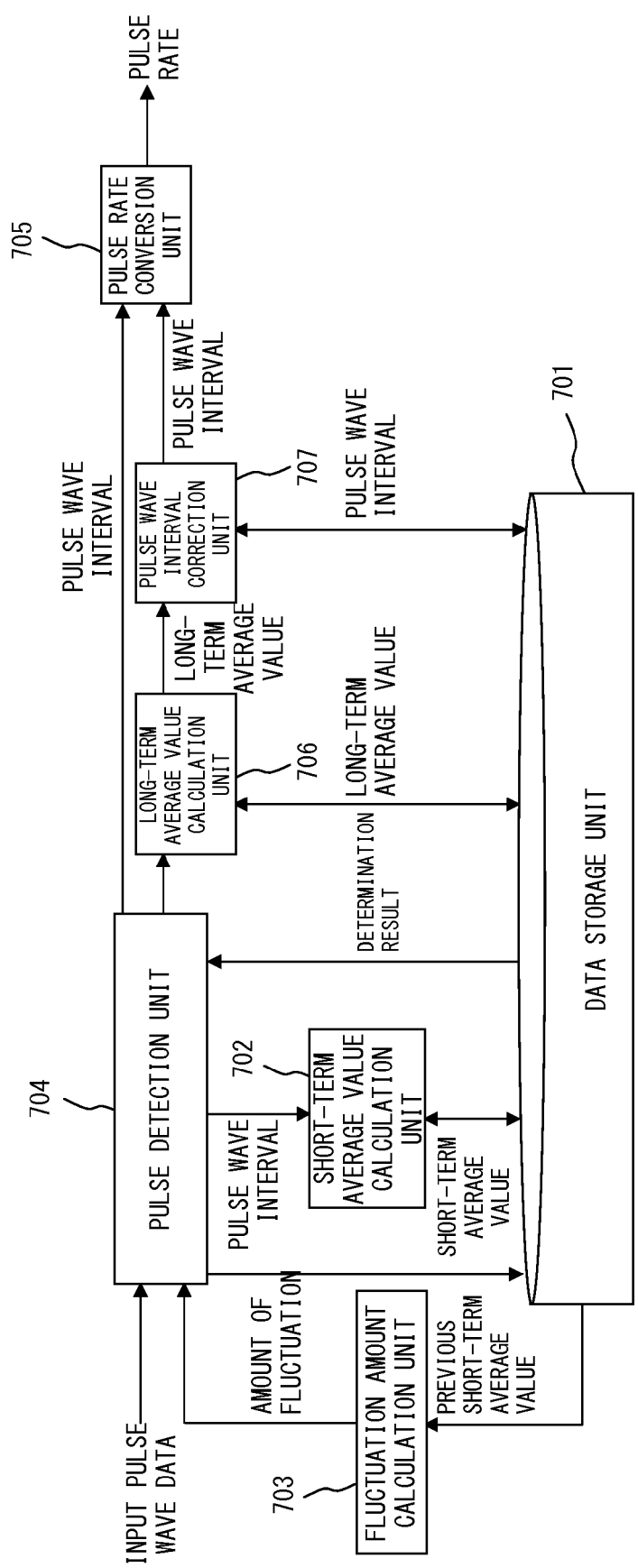
FIG. 8 shows the principle of the pulse rate counting device according to the fourth embodiment of the present invention.

FIG. 8 shows the principle of the pulse rate counting device according to the fourth embodiment of the present invention.

The pulse rate counting device according to the fourth embodiment of the present invention includes a data storage unit 701, a short-term average value calculation unit 702, a fluctuation amount calculation unit 703, a pulse detection unit 704, a pulse rate conversion unit 705, a long-term average value calculation unit 706, and a pulse wave interval correction unit 707.

As compared with the pulse rate counting device according to the first embodiment of the present invention, the pulse rate counting device according to the fourth embodiment is different in providing the long-term average value calculation unit 706 and the pulse wave interval correction unit 707.

The data storage unit 701, the short-term average value calculation unit 702, the fluctuation amount calculation unit 703, the pulse detection unit 704, and the pulse rate conversion unit 705 perform processes similar to those performed by the corresponding units of the pulse rate counting device according to the first embodiment of the present invention.

The long-term average value calculation unit 706 obtains an average value (long-term average value) of a pulse wave interval for about 10 previous seconds which is longer than a period in which a short-term average value of a pulse wave interval to be next obtained is calculated. While the short-term average value indicates a small change, the long-term average value indicates a change of a rough ascending or descending tendency of a pulse wave interval.

The pulse wave interval correction unit 707 corrects a pulse wave interval after detecting a sudden change in a value of a pulse wave interval from a time change amount of a long-term average value or a difference between a short-term average value and a long-term average value.

The pulse rate counting device according to the fourth embodiment obtains a long-term average value and uses both the long-term average value and the short-term average value, thereby correcting the obtained pulse wave interval. Thus, the accuracy of pulse rate detection can be improved.

FIG. 9 shows the principle of the pulse rate counting device according to the fifth embodiment of the present invention.

The pulse rate counting device according to the fifth embodiment of the present invention includes a data storage unit 801, a short-term average value calculation unit 802, a fluctuation amount calculation unit 803, a pulse detection unit 804, a pulse rate conversion unit 805, and a reliability display unit 806.

The data storage unit 801, the short-term average value calculation unit 802, the fluctuation amount calculation unit 803, the pulse detection unit 804, and the pulse rate conversion unit 805 perform processes similar to those performed by the corresponding units of the pulse rate counting device according to the first embodiment of the present invention.

As compared with the pulse rate counting device according to the first embodiment, the pulse rate counting device according to the fifth embodiment is different in that it is provided with the reliability display unit 806.

The reliability display unit 806 calculates and outputs the reliability of the pulse wave data depending on the amount of fluctuation input from the fluctuation amount calculation unit 803.

The pulse rate counting device according to the fifth embodiment allows a user to be informed of the reliability of the obtained pulse rate by calculating the reliability of the pulse wave data.

Figure 10:
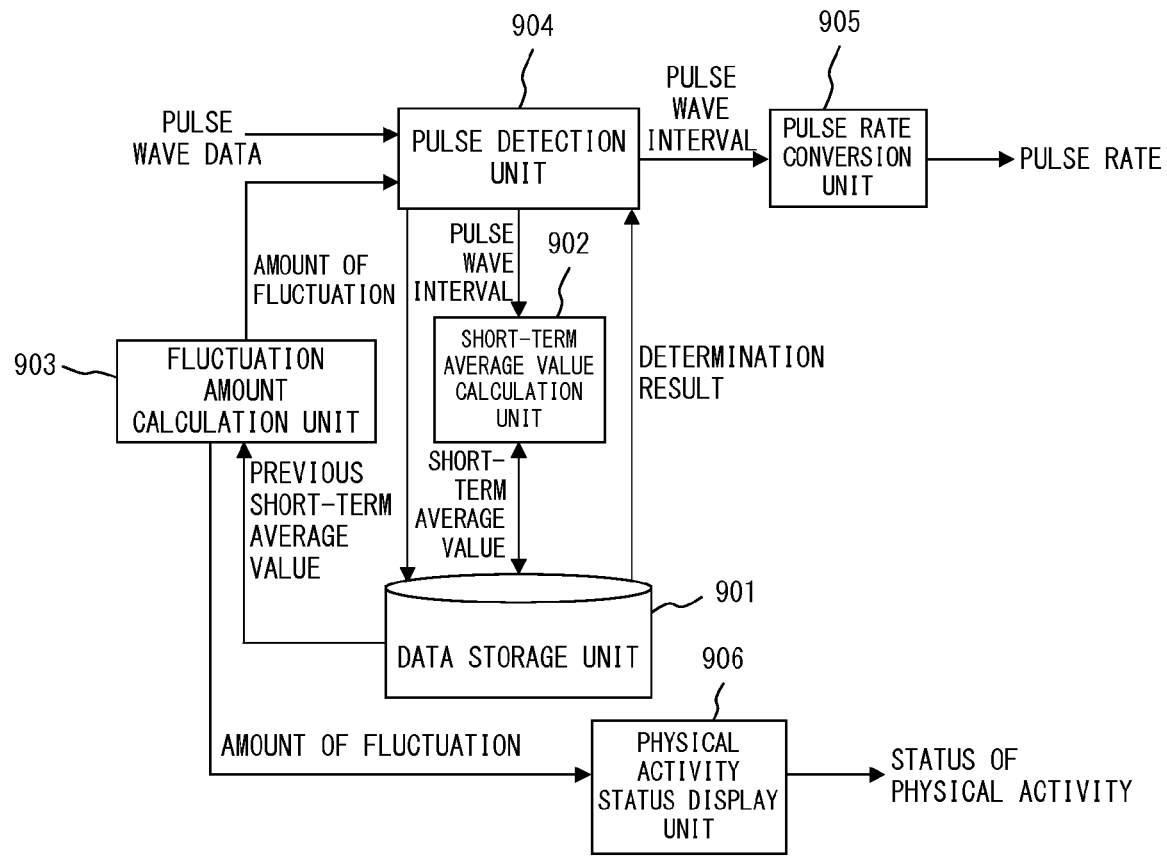
FIG. 10 shows the principle of the pulse rate counting device according to the sixth embodiment of the present invention.

FIG. 10 shows the principle of the pulse rate counting device according to the sixth embodiment of the present invention.

The pulse rate counting device according to the sixth embodiment includes a data storage unit 901, a short-term average value calculation unit 902, a fluctuation amount calculation unit 903, a pulse detection unit 904, a pulse rate conversion unit 905, and a physical activity status display unit 906.

The data storage unit 901, the short-term average value calculation unit 902, the fluctuation amount calculation unit 903, the pulse detection unit 904, and the pulse rate conversion unit 905 perform processes similar to those performed by the corresponding units of the pulse rate counting device according to the first embodiment.

As compared with the pulse rate counting device according to the first embodiment, the pulse rate counting device according to the sixth embodiment is different in that it is provided with the physical activity status display unit 906.

The physical activity status display unit 906 calculates and outputs the status of physical activity depending on the amount of fluctuation input from the fluctuation amount calculation unit 903.

The pulse rate counting device according to the sixth embodiment calculates the status of physical activity, thereby allowing a user to be informed of the status of the user.

Figure 11:
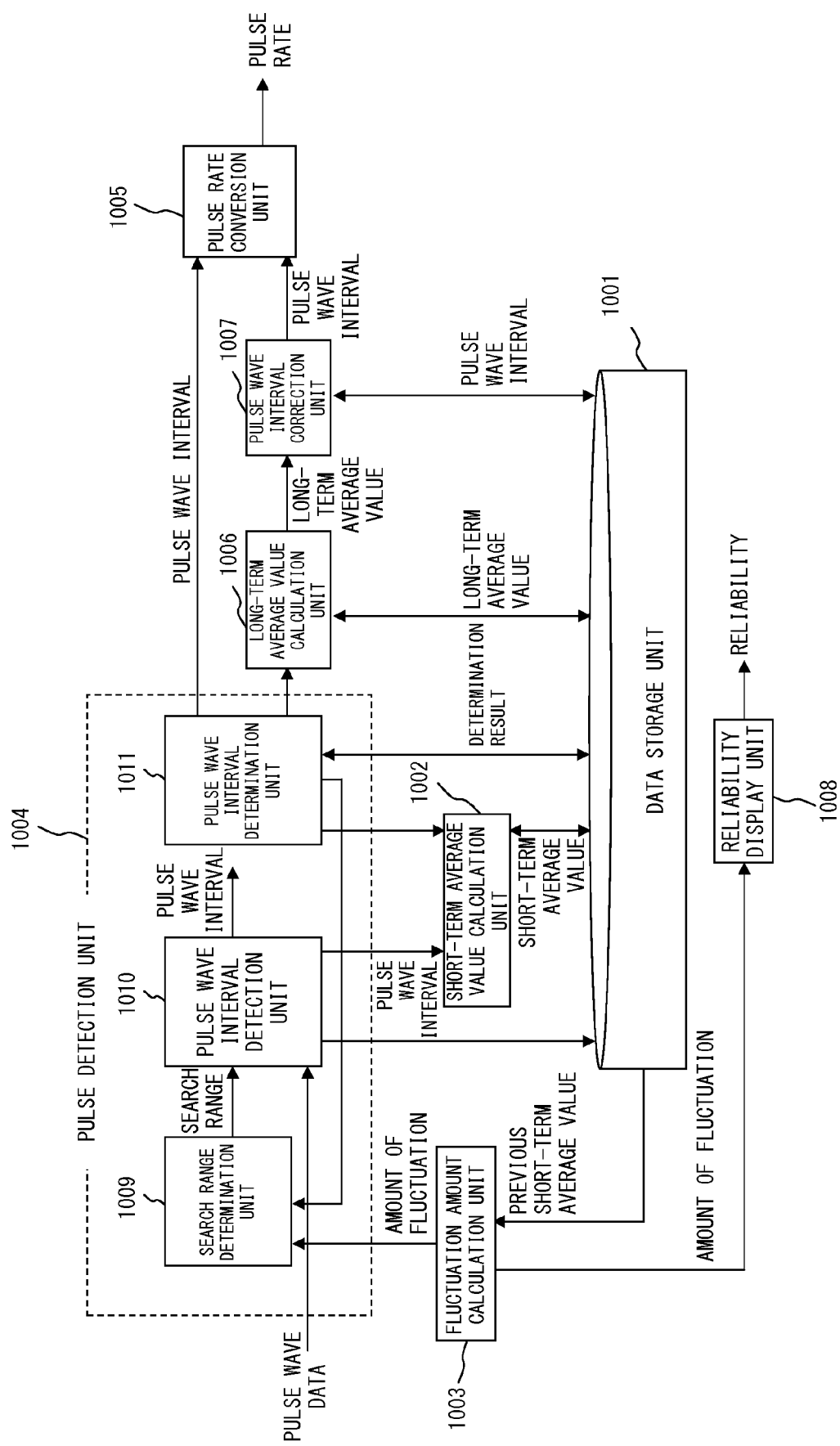
FIG. 11 shows the principle of the pulse rate counting device according to the seventh embodiment of the present invention.

FIG. 11 shows the principle of the pulse rate counting device according to the seventh embodiment of the present invention.

The pulse rate counting device according to the seventh embodiment of the present invention includes a data storage unit 1001, a short-term average value calculation unit 1002, a fluctuation amount calculation unit 1003, a pulse detection unit 1004, a pulse rate conversion unit 1005, a long-term average value calculation unit 1006, a pulse wave interval correction unit 1007, and a reliability display unit 1008.

The pulse detection unit 1004 includes a search range determination unit 1009, a pulse wave interval detection unit 1010, and a pulse wave interval determination unit 1011.

The data storage unit 1001 stores various types of data used by the pulse rate counting device. FIG. 12 shows an example of data stored in the data storage unit 1001.

The short-term average value calculation unit 1002 calculates an average value from the pulse wave interval for the pulse waves in some previous seconds before the pulse wave interval to be obtained next.

In calculating the average value, the pulse wave interval to be used can be specified by time such as a pulse wave interval of the pulse waves in the two previous seconds, or by number such as the previous five pulse wave intervals. For example, when n previous pulse wave intervals are used, the short-term average value is calculated by the following equation (1) where AAI(i) indicates the pulse wave interval at time i.

$$\text{short-term average value }(i) = \left(\sum_{j=1}^{n} AAI(i-j)\right)/n \quad (1)$$

When the pulse wave interval is specified by the number of seconds, the number of pulse wave intervals to be used on an average is not constant.

In addition, using the amount of fluctuation and the pulse wave interval determination result described later, the following processes can be performed when a short-term average value is calculated.

A pulse wave interval with a large amount of fluctuation is not used for calculating a short-term average value.

A pulse wave interval searched again is not used for calculating a short-term average value.

A corrected pulse wave interval by a long-term average value is not used for calculating a short-term average value.

A result of the calculated short-term average value is stored in the data storage unit 1001.

The fluctuation amount calculation unit 1003 calculates a amount of fluctuation corresponding to the fluctuation of pulse wave data from the absolute value of the difference between the previous short-term average value and pulse wave interval value.

The amount of fluctuation is obtained by the following equation (2).

$$\text{amount of fluctuation} = \left(\sum_{j=1}^{n} \frac{|\text{short-term average value }(i-j) - AAI(i-j)|}{\text{short-term average value }(i-j)}\right)/n \quad (2)$$

Also in the equation (2) above, a constant such as n=5 as in calculating a short-term average value can be used, or a value changed by the number of seconds such as the number of pulses in the 2 previous seconds can be used.

When the pulse wave data is input to the pulse detection unit 1004, the search range determination unit 1009 of the pulse detection unit 1004 determines the search range of the pulse wave interval to be next obtained on the basis of the short-term average value and the amount of fluctuation The search range of the pulse wave interval to be next obtained is set as a search range by shifting the "width of the search range" by a "shift width" by centering the pulse wave interval prediction value. The pulse wave interval prediction value can be, for example, a short-term average value, a pulse wave interval obtained immediately before, or a long-term average value.

For example, a short-term average value, a pulse wave interval obtained previously before, or a long-term average value described later.

The width of a search range is obtained by the following equation:

width of search range=$AAI(i-1) \times 0.5 \times (1+\text{amount of fluctuation})$ (3)

As described above, the width of a search range is calculated from the previous pulse wave interval and amount of fluctuation.

The shift width can be obtained by the following equation:

shift amount=(short-term average value $(i)$−short-term average value $(i-1)$)$\times \alpha$ (4)

where $\alpha$ indicates a coefficient of about 0.1~0.5.

Therefore, the search range is calculated as follows:

search range=(pulse wave interval prediction value+shift amount)±search range width (5)

The pulse wave interval detection unit 1010 detects a detection point as a reference of the pulse wave interval in the search range in the pulse wave data, and outputs the interval between the previously detected detection point and the currently detected detection point as a pulse wave interval to the pulse wave interval determination unit 1011 and the short-term average value calculation unit 1002. The detection point can be obtained as, for example;

minimum value (or maximum value) of pulse wave data minimum value (or maximum value) of difference data of pulse wave data minimum value (or maximum value) of secondary difference data of pulse wave data auto-correlation of pulse wave data auto-correlation of difference data of pulse wave data auto-correlation of secondary difference data of pulse wave data, and others The pulse wave interval determination unit 1011 determines whether or not the pulse wave interval calculated by the pulse wave interval detection unit 1010 is an appropriate value. A pulse wave interval regarded as appropriate is stored in the data storage unit 1001.

In determining whether or not the interval is appropriate, for example, the following condition is considered:

a value in a range within ±25% of the previously obtained pulse wave interval a value in a range within ±15% of the previously obtained short-term average value a minimum value equal to or smaller than a threshold (a maximum value equal to or larger than a threshold)

a correlation equal to or smaller than a threshold no other minimum value (maximum value) at ½ or ⅓ position within the currently obtained pulse wave interval other high-correlation pulse wave intervals at ½ or ⅓ position within the currently obtained pulse wave interval These conditions can be solely used or can be used in combination with others.

When the pulse wave interval determination unit 1011 determines that data is not appropriate, the determination result is transmitted to the search range determination unit 1009, the search range determination unit 1009 sets a search range again, and detects the pulse wave interval again.

In setting a search range again, a new search range is expanded over the previous search range. An amount of fluctuation is also used when the search range is expanded. When the amount of fluctuation is large, the expansion is more largely performed. The pulse wave interval detected after setting again the search range is stored as a pulse wave interval searched again in the data storage unit 1001.

The pulse rate conversion unit 1005 performs conversion into a heart rate from the obtained pulse wave interval and the sampling frequency of pulse wave data. For example, when a heart rate per minute is obtained, the following equation is used.

heart rate=60 (sec)×sampling frequency/pulse wave interval (6)

In the present embodiment, the pulse wave data is data sampled by a predetermined sampling frequency, and the pulse wave interval is obtained as the number of pieces of data in the pulse wave interval. Therefore, the heart rate per minute is obtained by the equation (6).

When a pulse wave interval is obtained in a time unit such as a second, the heart rate per minute is calculated by the following equation:

heart rate=60 (seconds/minute)/pulse wave interval (seconds)

The reliability display unit 1008 calculates and displays the reliability of the pulse wave data depending on the amount of fluctuation or the pulse wave interval. For example, in the section in which the reliability is calculated, the reliability is calculated and displayed using one of the following conditions.

a value in a range within ±25% of the previously obtained pulse wave interval a value in a range within ±15% of the previously obtained short-term average value a minimum value equal to or smaller than a threshold (a maximum value equal to or larger than a threshold)

a correlation equal to or larger than a threshold a amount of fluctuation equal to or smaller than a threshold a pulse wave interval searched again in the candidates for a pulse wave interval used in calculating a short-term average value equal to or smaller than 30% not a pulse wave interval with a corrected long-term average value

In addition, the method of displaying the reliability can be, in the above-mentioned conditions, represented by a 3-value display, that is, a value higher than 30% as satisfying the condition, a value lower than 70%, a normal value otherwise, can be a determination of "low" when only one condition is not satisfied, a determination of "high" when all conditions are satisfied, or can be represented by a value of 0 through 100 so that 100 points can be acquired when all conditions are satisfied after adding up a value of each condition.

In the present embodiment, if there is a physical activity status display unit instead of the reliability display unit 1008, it calculates and displays the status of physical activity. The status of physical activity can be a amount of fluctuation itself, or a amount of fluctuation can be divided by a threshold into three values (hard activity, normal activity, and light activity) or two values (hard activity and light activity). A value similar to reliability can be used.

The long-term average value calculation unit 1006 obtains an average value from a pulse wave interval for a time longer than when the short-term average value of a pulse wave interval to be obtained next, for example, about the previous 10 seconds, is calculated. The long-term average value indicates a change of a rough increasing or decreasing tendency of a pulse wave interval while a short-term average value indicates a small change. When a long-term average value is obtained, the number of seconds such as the previous 10 seconds can be specified as a pulse wave interval, or the number of pulses such as the previous 30 pulses can be specified as a pulse wave interval. When the long-term average value is obtained, the value can be calculated only when the amount of fluctuation calculated by the fluctuation amount calculation unit 1003 exceeds a threshold. The long-term average value calculation unit 1006 stores the calculated long-term average value in the data storage unit 1001.

The pulse wave interval correction unit 1007 detects a sudden change of a pulse wave interval from change-with-time amount of a long-term average value, or a difference between the short-term average value and the long-term average value, and corrects the pulse wave interval. When a change-with-time amount of a long-term average value is used, for example, assume that the following equation holds.

$$\text{change-with-time amount } (i) \text{ of long-term average value} = (\text{long-term average value } (i) - AAI(i)) - (\text{long-term average value } (i-1) - AAI(i-1)) \quad (7)$$

Correction is performed when the following equations hold:

$$\text{change-with-time amount } (i) \text{ of long-term average value/long-term average value } (i) > 0.1 \quad (8)$$

and $$\text{change-with-time amount } (i-1) \text{ of long-term average value/long-term average value } (i-1) > 0.1 \quad (9)$$

When a pulse wave interval AAI(i) is obtained, and if the difference between a short-term average value and a long-term average value is used, correction is performed when, for example, the following equation holds:

$$(\text{long-term average value } (i-1) - \text{short-term average value } (i-1))/\text{long-term average value } (i-1) > 0.1 \quad (10)$$

In addition, a method of performing correction by the pulse wave interval correction unit 1007 can be realized by the following equations.

$$AAI_c(i) = \text{long-term average value } (i) \quad (11)$$

$$AAI_c(i) = \text{short-term average value } (i) \quad (12)$$

$$AAI_c(i) = \alpha \Delta AAI(i) + \beta \times \text{long-term average value } (i) \quad (13)$$

where $\alpha + \beta = 1.0 \quad 0.0 < \alpha < 1.0$

In addition, when a correction condition is continuously satisfied, the following equation can be used.

$$AAI_c(i) = \gamma \Delta \text{long-term average value } (i) \quad (1.0 \leq \gamma \leq 2.0) \quad (14)$$

When correction is performed using the above-mentioned long-term average value, the result is stored as a corrected pulse wave interval in the data storage unit 1001.

Described next is a process for obtaining a pulse rate.

Figure 13:
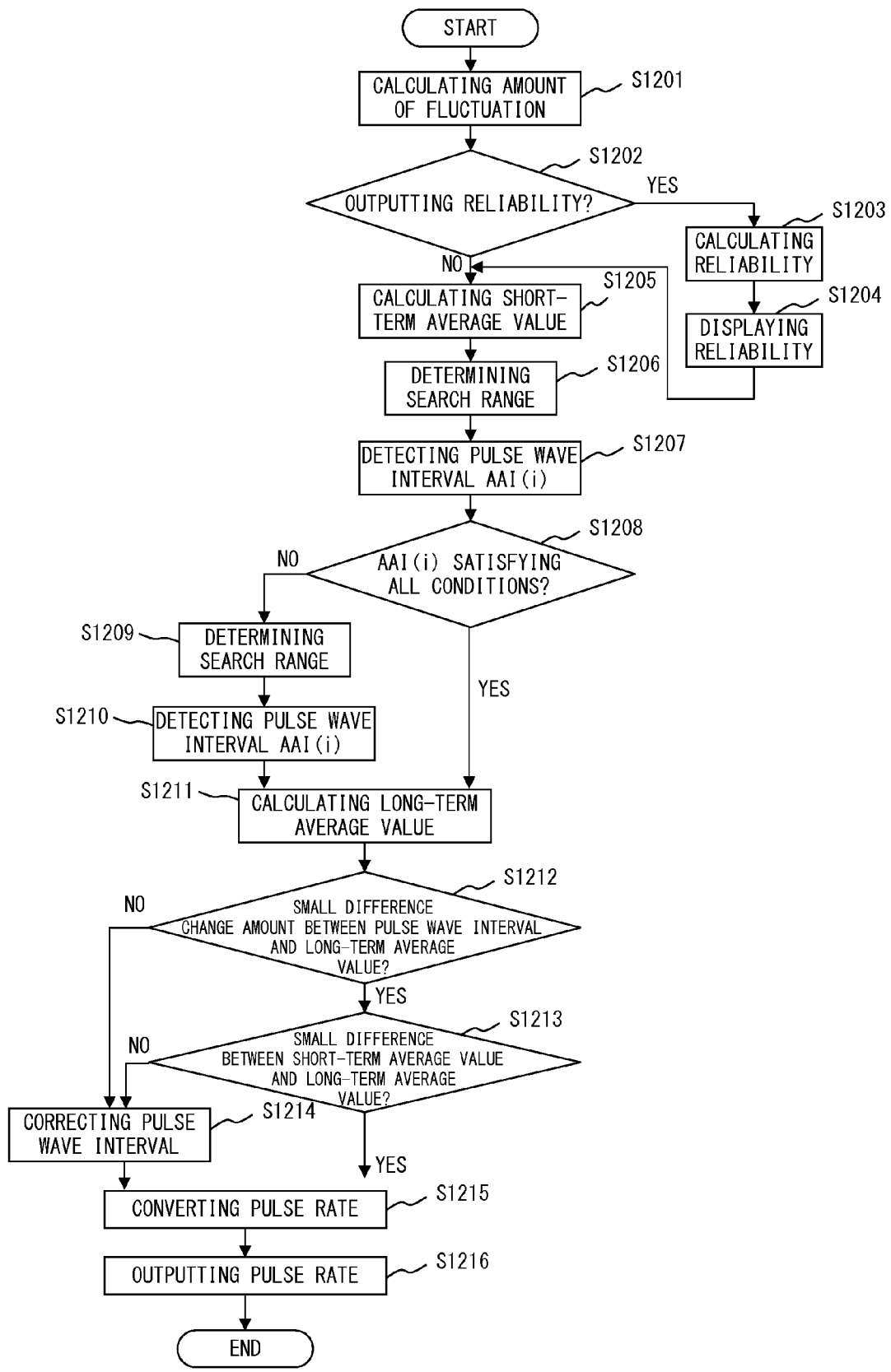
FIG. 13 is a flowchart of the process of the pulse rate counting device according to the seventh embodiment of the present invention.

FIG. 13 is a flowchart of the process of the pulse rate counting device according to the seventh embodiment of the present invention.

In step S1201, the fluctuation amount calculation unit 1003 calculates a amount of fluctuation from the past short-term average value and the past pulse wave interval, and outputs the amount of fluctuation to the search range determination unit and the reliability display unit.

In step S1202, it is determined whether or not the reliability is output on the basis of a predetermined setting. When it is output, control is passed to step S1203. If it is not output, control is passed to step S1205.

In step S1203, the reliability display unit 1008 calculates the reliability on the basis of the input amount of fluctuation.

In step S1204, the reliability display unit 1008 output the calculated reliability.

In step S1205, the short-term average value calculation unit 1002 calculates a short-term average value as an average value of pulse wave intervals of some previous pulses, and stores a short-term average value in the data storage unit 1001.

In step S1206, the search range determination unit 1009 calculates a search range on the basis of the short-term average value and the amount of fluctuation, and outputs the search range to the pulse wave interval detection unit 1010.

In step S1207, the pulse wave interval detection unit 1010 detects a detection point in the search range of pulse wave data, and outputs to the pulse wave interval determination unit 1011 the pulse wave interval as an interval between the previously obtained detection point and the currently obtained detection point.

In step S1208, the pulse wave interval determination unit 1011 determines whether or not an input pulse wave interval is appropriate, that is, whether or not predetermined conditions are satisfied. If the conditions are satisfied, the pulse wave interval is output to the pulse rate conversion unit 1005 and the long-term average value calculation unit 1006, and control is passed to step S1211. If the conditions are not satisfied, the determination result of inappropriateness is output to the search range determination unit 1009, and control is passed to step S1209.

In step S1209, upon receipt of the determination result of inappropriate pulse wave interval, the search range determination unit 1009 sets again a range larger than the previously calculated search range as a search range, and outputs the range to the pulse wave interval detection unit 1010.

In step S1210, the pulse wave interval detection unit 1010 detects a detection point in the search range set again of the pulse wave data, and outputs the pulse wave interval as a interval between the previously obtained detection point (not the detection point obtained in step S1207, but the previously obtained detection point in step S1207) and the currently obtained detection point to the pulse rate conversion unit 1005 and the long-term average value calculation unit 1006 through the pulse wave interval determination unit 1011.

In step S1211, the long-term average value calculation unit 1006 calculates a long-term average value of a pulse wave interval, and stores the long-term average value in the data storage unit 1001 and outputs the pulse wave interval correction unit 1007.

In step S1212, the pulse wave interval correction unit 1007 determines whether or not an amount of difference change between the pulse wave interval and the long-term average value is small. Practically, it is determined whether or not the equations (8) and (9) are satisfied. When the amount is small, control is passed to step S1213. Otherwise, control is passed to step S1214.

In step S1213, it is determined whether or not the difference between the short-term average value and the long-term average value is small. Practically, it is determined whether or not the equation (10) above is satisfied. When it is small, control is passed to step S1215. Otherwise, control is passed to step S1214.

In step S1214, the pulse wave interval correction unit 1007 corrects a pulse wave interval. A correct method can be in accordance with the equations (11) through (14). The pulse wave interval correction unit 1007 stores the corrected pulse wave interval in the data storage unit 1001, and outputs the data to the pulse rate conversion unit 1005. When the corrected pulse wave interval is stored in the data storage unit 1001, how the correction is performed is also recorded.

In step S1215, the pulse rate conversion unit 1005 calculates the pulse rate on the basis of the pulse wave interval.

In step S1216, the pulse rate conversion unit 1005 outputs a calculated pulse rate. It also can output the pulse wave interval in addition to the pulse rate.

In the above-mentioned embodiment, the pulse wave data is input from the pulse wave sensor etc. to the pulse rate counting device. The pulse wave interval and the pulse rate counted by the pulse rate counting device can be output to the display device provided for the pulse rate counting device, or to a device connected by wireless, over a network, etc.

The pulse rate counting device according to an embodiment of the present invention, uses the fluctuation of pulses as an amount of fluctuation, and determines the search range of a detection point on the basis of the amount of fluctuation. Therefore, a pulse rate can be detected with high accuracy although the pulse waves fall into fluctuation due to physical activities.

Furthermore, since only a pulse wave sensor is used and other sensors such as a physical activity sensor etc. are not used, the necessary cost can be reduced.

Furthermore, the accuracy in detecting pulses can be improved by obtaining a long-term average value of pulse wave intervals, using a long-term average value and a short-term average value, and correcting the obtained pulse wave interval.

In addition, since only the process of searching a detection point in a detection range is required, the computational complexity can be reduced than in searching a detection point in the entire input pulse wave data. Obviously, necessary power consumption can be reduced.

The embodiments of the present invention are described above with reference to the attached drawings, but the pulse rate counting device according to the present invention is not limited to the above-mentioned embodiments so far as the functions of the device can be realized, and it is obvious that the device can be a single unit, a system including a plurality of devices, an integrated device, and a system capable of performing a process over a network such as a LAN, WAN, etc.

The device according to the present invention can also be realized by a system configured by a CPU, memory such as ROM and RAM, an input device, an output device, an external record device, a medium drive device, and a network connection device. That is, it is obvious that the present invention can be attained also by providing memory such as ROM and RAM recording a program code of software for realizing the system, an external record device, and a portable record medium according to the above-mentioned embodiments for the pulse rate counting device, and the computer of the pulse rate counting device reading and executing the program code.

In this case, the program code itself read from a portable record medium etc. realizes new functions of the present invention, and the portable record medium etc. recording the program code configures the present invention.

A portable record medium for providing a program code can be, for example, a flexible disk, a hard disk, an optical disk, a magneto optical disk, CD-ROM, CD-R, DVD-ROM, DVD-RAM, magnetic tape, a non-volatile memory card, a ROM card, various record media for recording data through e-mail and a network connection device (that is, a communication line) for PC communication, etc.

The functions of the above-mentioned embodiments can be realized by a computer (information processing device) executing a program code read to the memory, and also can be realized by all or a part of the practical process by the OS etc. operating on the computer according to the instruction of the program code.

Furthermore, after a program (data) provided from a program code read from a portable record medium and a program (data) provider is written to the memory provided for a feature expansion board inserted into the computer and a feature expansion unit connected to the computer, a CPU etc. provided for the feature expansion board and the feature expansion unit performs all or a part of the actual process according to the instruction of the program code, and the functions of the above-mentioned embodiments can be realized by the process.

That is, the present invention is not limited to the above-mentioned embodiments, but can have various configurations or modes within the scope of the gist of the present invention.

What is claimed is:

1. A pulse rate counting device, comprising:
    a short-term average value calculation unit receiving input of pulse wave data acquired from a change of bloodstream and calculating an average interval of predetermined previous pulses;
    a fluctuation value calculation unit calculating a fluctuation value that is an average of absolute values of differences between the average interval and a predetermined number of previous actual pulse wave intervals;
    a search range determination unit calculating a width of a search range of a detection point as a reference of a next pulse wave interval by multiplying a previous pulse wave interval by the fluctuation value, calculating an amount of displacement on a basis of a time change of the average interval, and determining as a search range a range including an appearance prediction value of a next detection point calculated from the average interval and indicated by the width of a search range from a starting point that is a sum of the amount of displacement and the appearance prediction value; and
    a pulse wave interval detection unit detecting the detection point in the determined search range, and outputting an interval between a predetermined detection point and a current detection point as a pulse wave interval.

2. The device according to claim 1, further comprising a pulse wave interval correction unit correcting a detected pulse wave interval when a difference between a second average interval as an average for a longer time than a pulse wave on which the average interval is calculated and the detected pulse wave interval, or a difference between the average interval and the second average interval is larger than a threshold.

3. The device according to claim 1, further comprising a pulse wave interval determination unit determining whether or not the pulse wave interval satisfies a predetermined condition.

4. The device according to claim 3, wherein the search range determination unit determines a search range again when the pulse wave interval determination unit determines that the pulse wave interval does not satisfy a predetermined condition.

5. The device according to claim 3, further comprising a reliability calculation unit calculating reliability of the pulse wave data on a basis of the fluctuation value or the pulse wave interval.

6. The device according to claim 3, further comprising a physical activity status unit calculating a status of physical activity of a user on a basis of the fluctuation value or the pulse wave interval.

7. A pulse rate counting method, comprising:
    receiving, using a computer, input of pulse wave data acquired from a change of bloodstream and calculating an average interval of predetermined previous pulses;

calculating, using the computer, a fluctuation value that is an average of absolute values of differences between the average interval and a predetermined number of previous actual pulse wave intervals;

calculating, using the computer, a width of a search range of a detection point as a reference of a next pulse wave interval by multiplying a previous pulse wave interval by the fluctuation value, calculating an amount of displacement on a basis of a time change of the average interval, and determining as a search range a range including an appearance prediction value of a next detection point calculated from the average interval and indicated by the width of the search range from a starting point that is a sum of the amount of displacement and the appearance prediction value; and detecting, using the computer, the detection point in the determined search range, and outputting an interval between a predetermined detection point and a current detection point as a pulse wave interval.

8. The method according to claim 7, further comprising correcting, using the computer, a detected pulse wave interval when a difference between a second average interval as an average for a longer time than a pulse wave on which the average interval is calculated and the detected pulse wave interval, or a difference between the average interval and the second average interval is larger than a threshold.

9. The method according to claim 7, further comprising determining, using the computer, whether or not the pulse wave interval satisfies a predetermined condition.

10. The method according to claim 7, further comprising determining, using the computer, a search range again when the pulse wave interval does not satisfy a predetermined condition.

11. A tangible non-transitory record medium containing computer executable instructions to perform a method, the method comprising:

receiving input of pulse wave data acquired from a change of bloodstream and calculating an average interval of predetermined previous pulses;

calculating a fluctuation value that is an average of absolute values of differences between the average interval and a predetermined number of previous actual pulse wave intervals;

calculating a width of a search range of a detection point as a reference of a next pulse wave interval by multiplying a previous pulse wave interval by the fluctuation value, calculating an amount of displacement on a basis of a time change of the average interval, and determining as a search range a range including an appearance prediction value of a next detection point calculated from the average interval and indicated by the width of a search range from a starting point that is a sum of the amount of displacement and the appearance prediction value; and detecting the detection point in the determined search range, and outputting an interval between a predetermined detection point and a current detection point as a pulse wave interval.

12. The record medium according to claim 11, the method further comprising correcting a detected pulse wave interval when a difference between a second average interval as an average for a longer time than a pulse wave on which the average interval is calculated and the detected pulse wave interval, or a difference between the average interval and the second average interval is larger than a threshold.

13. The record medium according to claim 11, further comprising the procedure of determining whether or not the pulse wave interval satisfies a predetermined condition.

14. The record medium according to claim 13, the method further comprising determining a search range again when the pulse wave interval does not satisfy a predetermined condition.

* * * * *